US010786563B2

(12) United States Patent
Lv et al.

(10) Patent No.: US 10,786,563 B2
(45) Date of Patent: Sep. 29, 2020

(54) HEAT-RESISTANT PROTECTIVE AGENT, ROOM-TEMPERATURE-PRESERVED LIVE CLASSICAL SWINE FEVER VACCINE, AND PREPARATION METHOD AND APPLICATION THEREOF

(71) Applicant: JIANGSU ACADEMY OF AGRICULTURAL SCIENCES, Nanjing (CN)

(72) Inventors: Fang Lv, Nanjing (CN); Yu Lu, Nanjing (CN); Jibo Hou, Nanjing (CN); Yanhong Zhao, Nanjing (CN); Bihua Deng, Nanjing (CN); Jinqiu Zhang, Nanjing (CN); Xiaoyan Zhang, Nanjing (CN); Xiaoxin Zuo, Nanjing (CN)

(73) Assignee: JIANGSU ACADEMY OF AGRICULTURAL SCIENCES, Nanjing (CN)

( * ) Notice: Subject to any disclaimer, the term of this patent is extended or adjusted under 35 U.S.C. 154(b) by 0 days.

(21) Appl. No.: 16/333,724

(22) PCT Filed: Sep. 21, 2017

(86) PCT No.: PCT/CN2017/102667
§ 371 (c)(1),
(2) Date: Mar. 15, 2019

(87) PCT Pub. No.: WO2019/028976
PCT Pub. Date: Feb. 14, 2019

(65) Prior Publication Data
US 2019/0269772 A1 Sep. 5, 2019

(30) Foreign Application Priority Data
Aug. 8, 2017 (CN) .......................... 2017 1 0670177

(51) Int. Cl.
| *A61K 39/12* | (2006.01) |
| *A61K 9/08* | (2006.01) |
| *A61K 47/10* | (2017.01) |
| *A61K 9/00* | (2006.01) |
| *A61K 47/18* | (2017.01) |
| *A61K 47/26* | (2006.01) |
| *A61K 47/42* | (2017.01) |
| *A61P 31/14* | (2006.01) |
| *A61K 39/00* | (2006.01) |

(52) U.S. Cl.
CPC ............ *A61K 39/12* (2013.01); *A61K 9/0019* (2013.01); *A61K 9/08* (2013.01); *A61K 47/10* (2013.01); *A61K 47/183* (2013.01); *A61K 47/26* (2013.01); *A61K 47/42* (2013.01); *A61P 31/14* (2018.01); *A61K 2039/525* (2013.01); *A61K 2039/552* (2013.01); *C12N 2770/24334* (2013.01)

(58) Field of Classification Search
None
See application file for complete search history.

(56) References Cited

U.S. PATENT DOCUMENTS

2012/0052124 A1* 3/2012 Kaplan ................ A61K 9/0019
424/489

FOREIGN PATENT DOCUMENTS

| CN | 105999284 | * 10/2016 |
| WO | WO16157208 | * 10/2016 |

OTHER PUBLICATIONS

Translation Specification of CN105999284, tanslated from Espacenet (EPO) webpage on Feb. 12, 2020.*

* cited by examiner

*Primary Examiner* — Benjamin P Blumel
(74) *Attorney, Agent, or Firm* — CBM Patent Consulting, LLC

(57) ABSTRACT

A thermostable formula comprises the following components in percentage by mass: 1% to 5% raffinose, 5% to 10% maltose, 15% to 30% saccharose, 1% to 5% lactose, 1% to 5% glucose, 0.1% to 1.5% polysorbate 80, 0.1% to 0.5% polyethylene glycol 8000, 0.5% to 3% tyrosine, 3% to 6% silk fibroin, and the balance of water for injection. It further discloses a room-temperature-preserved live classical swine fever vaccine and a preparation method thereof, wherein the live classical swine fever vaccine is obtained by mixing the thermostable formula with a live classical swine fever virus solution and then carrying out gradient vacuum drying. The vaccine prepared according to the present invention has a dried foam appearance and presents a glass-layer like structure under a scanning electron microscope, has a glass transition temperature up to more than 50° C.

8 Claims, 1 Drawing Sheet

HEAT-RESISTANT PROTECTIVE AGENT, ROOM-TEMPERATURE-PRESERVED LIVE CLASSICAL SWINE FEVER VACCINE, AND PREPARATION METHOD AND APPLICATION THEREOF

TECHNICAL FIELD

The present invention belongs to the field of vaccine preparation, specifically relates to a thermostable formula, a room-temperature-preserved live classical swine fever vaccine, and a preparation method and an application thereof, and more particularly, relates to a room-temperature-preserved live classical swine fever vaccine and a preparation method thereof.

BACKGROUND

Classical swine fever (CSF) is an acute, febrile and highly contact infectious disease caused by classical swine fever virus (CSFV) of flaviviridae pestivirus with wide epidemicity and high mortality, causing huge potential safety hazard and economic loss to the pig industry. At present, a live CSF cell culture origin vaccine and a CSF Rabbit spleen vaccine play a better role in preventing CSF in the market, both of which are based on a C strain.

CSFV is very sensitive to heat, and it is reported that CSFV has a half-life of 3 hours only at 37° C. At current, the commonly used classical swine fever vaccine is mainly prepared by lyophilization, and the lyophilization protective agents commonly used in the market are simple in composition and mostly contain saccharose, gelatin, thiourea, bovine serum albumin, lactoalbumin hydrolysate, phosphate and other components. The vaccine has limited heat resistance and can only be preserved for 7 days to 10 days at 37° C., or preserved for a long time at −15° C., or preserved for 1 year to 2 years at 2° C. to 8° C. Once a cold chain breaks, a valence of the product is lost by more than 50% or even lost completely in a few hours at a normal temperature. Meanwhile, since an ice crystal formed in a freezing process causes mechanical damages to a virus capsule or a cell wall to different degrees, the virus activity will be greatly reduced. Therefore, reducing the drying loss of the vaccine and improving the heat resistance of the vaccine to ensure the vaccine quality are key technologies to give full play to immune efficacy. In recent years, many researchers have been studying and improving heat-resistant technologies, such as spray drying and biomimetic mineralization, but all these technologies are at lab study levels.

A sugar glass vaccine technology can prepare the vaccine into a glassy state, and the technology is mainly realized through a gradient vacuum drying process. In the process of reducing the vacuum gradient, high-viscosity sugar containing the vaccine is gradually solidified into a glass body through boiling, foaming and volatilization of water, and since non-reducing sugar is stable, the sugar glass wrapping the vaccine may not react with protein. The technology can be carried out at a normal temperature without freezing, thus avoiding the mechanical damage of ice crystal generated by "freezing" in the traditional lyophilization to the virus; moreover, due to the high sugar content and viscosity of the vaccine, the formed glassy state vaccine has a higher glass transition temperature and can be preserved for a long time excluding the room temperature or "cold chain" environment.

A glass transition temperature Tg is an important characteristic thermal parameter of a substance and is the temperature at which a substance changes from a glassy state to a highly elastic state. Below the Tg, a polymer is in a glassy state, a molecular chain and a chain segment cannot move, but atoms (or groups) that contribute a molecule vibrate at their equilibrium positions; and at the Tg, the molecular chain cannot move, but the chain segment begins to move, showing high elastic property, and when the temperature rises again, the whole molecular chain moves and shows viscous flow property. For dried vaccine, the higher the Tg is, the greater the difference between the Tg and the storage temperature is, and the more favorable the long-term preservation of the vaccine is.

Based on the above principle, a thickening agent needs to be added to increase the viscosity of the vaccine before gradient vacuum drying, and meanwhile, a decrease rate of vacuum degree should not be too fast, so as to ensure that foams can be generated during the drying process and the sample does not spray out from a bottle. Therefore, the formulation design should include the following categories: polyol, polymer, surfactant, amino acid and protein stabilizer. The polyol can replace water lost in hydration in the drying process to prevent denaturation of bioactive substance and can act as a thickening agent, the toughness thereof can support the formation and stability of foam, thus forming a dried foam structure. The commonly used foam components include: saccharose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, glycerol, L-sodium stibogluconate, etc. Most polyols and bioactive substances are prepared into a mixed solution with a concentration of 1 to 35%, 1.5 to 9%, or 10 to 25%.

The polymer mainly plays a protective role in the composition, when the polymer is used with the polyol, the viscosity of the component is increased, and the linear or branched stripe polymer can increase the strength of the dried foam structure in the present invention. Many polymers are highly water-soluble, so that they may not significantly hinder the reconstruction of dried foams. The surfactant mainly protects the surface tension during foam formation, so as to avoid denaturation of some bioactive components, foam stabilization, rapid reconstitution, etc. The surfactant may be a suitable ionic/nonionic detergent, Tween surfactant, Pluronic surfactant, etc. The addition of protein and amino acid is helpful to the antioxidation of dried product during long-term storage, and the commonly used proteins include bovine serum albumin, silk fibroin, etc.; and the amino acids include tyrosine, arginine, histidine, cysteine, etc.

In addition, it should be noted that the residual water content of the sugar glass vaccine should not be too high and should be controlled at 1% to 3%, and under this residual water condition, the vaccine can better keep a glassy state and be stable.

SUMMARY

Object of the present invention: a technical problem to be solved by the present invention is to provide a thermostable formula.

A technical problem to be further solved by the present invention is to provide a preparation method of the thermostable formula.

A technical problem to be further solved by the present invention is to provide an application of the thermostable formula in preparing a vaccine.

A technical problem to be further solved by the present invention is to provide an application of the thermostable formula in preparing a room-temperature-preserved live classical swine fever vaccine.

A technical problem to be finally solved by the present invention is to provide a preparation method of the room-temperature-preserved live classical swine fever vaccine.

Technical solutions: the object of the present invention is achieved through the following technical solutions: a thermostable formula comprise, but is not limited to, the following components in percentage by mass: 1% to 5% raffinose, 5% to 10% maltose, 15% to 30% saccharose, 1% to 5% lactose, 1% to 5% glucose, 0.1% to 1.5% polysorbate 80, 0.1% to 0.5% polyethylene glycol 8000, 0.5% to 3% tyrosine, 3% to 6% silk fibroin, and the balance of water for injection.

The thermostable formula comprise but is not limited to the following components in percentage by mass: 1.5% to 4% raffinose, 6% to 10% maltose, 20% to 25% saccharose, 2% to 4% lactose, 2% to 4% glucose, 0.5% to 1% polysorbate 80, 0.2% to 0.4% polyethylene glycol 8000, 1% to 2% tyrosine, 4% to 5% silk fibroin, and the balance of water for injection.

The present invention further comprises a preparation method of the thermostable formula, which comprises the following steps of:

1) dissolving raffinose, maltose, saccharose, lactose, glucose and polysorbate 80 in water and carrying out sterilization by high-pressure steam sterilization to obtain a solution 1;

2) dissolving polyethylene glycol 8000, tyrosine and silk fibroin in water, and carrying out sterilization by filtration to obtain a solution 2; and 3) mixing the solution 1 and the solution 2, and supplementing water to obtain the thermostable formula.

The present invention further comprises an application of the thermostable formula above in preparing a vaccine.

The present invention further comprises an application of the thermostable formula above in preparing a room-temperature-preserved live classical swine fever vaccine.

The present invention further comprises a preparation method of the room-temperature-preserved live classical swine fever vaccine, wherein a classical swine fever virus solution and the thermostable formula are uniformly mixed according to a volume ratio of 1 to 3:1 to prepare a live classical swine fever vaccine solution, and the live classical swine fever vaccine is obtained after gradient vacuum drying. During the drying process, the vacuum degree decreases step by step while the temperature is maintained at room temperature, the moisture volatilizes, the liquid becomes viscous and the boiling point decreases, and when the vacuum degree and the viscosity of the solution reach a certain threshold value, the solution begins to bubble and the surface area of moisture volatilization increases, thus accelerating the drying of the vaccine. The process has no freezing stage, thus preventing the ice crystal from damaging the virus.

Specifically, the gradient vacuum drying method is as follows.

The live classical swine fever vaccine solution is balanced for 0.5 hour to 2 hours at a normal temperature and a normal pressure, maintained for 0.5 hour to 1 hour at a vacuum degree of 500 mBar to 800 mBar and a temperature of 5° C. to 30° C., maintained for 0.5 hour to 2 hours at a vacuum degree of 80 mbar to 500 mbar and a temperature of 10° C. to 35° C., maintained for 0.5 hour to 2 hours at a vacuum degree of 30 mBar to 80 mBar and a temperature of 10° C. to 40° C., maintained for 8 hours to 12 hours at a vacuum degree of 0.01 mbar to 0.05 mbar and a temperature of 20° C. to 40° C., and maintained for 12 hours to 24 hours at a vacuum degree of 0.001 mbar to 0.01 mBar and a temperature of 20° C. to 40° C., to obtain a dried live classical swine fever vaccine.

The live classical swine fever vaccine prepared by the present invention is preserved for three months at 37° C. and for one year at 25° C.

The dried live classical swine fever vaccine presents a glass-layer like structure under a scanning electron microscope, and a glass transition temperature thereof reaches up to more than 50° C. The glass transition temperature reaches up to 65° C. to 70° C.

The classical swine fever virus solution is cellular poison (a C strain).

Beneficial effects: compared with the prior art, the present invention has the following advantages.

1. Because the thermostable formula according to the present invention has reasonable component collection, the live classical swine fever vaccine is heat-resistant and storable, the virus can be kept in a dormant state, and the life activities of virus in drying and storage periods are reduced;

2. The gradient vacuum drying technology in the present invention can avoid ice crystal damage, so that the loss in the preparation process of the live classical swine fever vaccine is minimized, and the activity of the classical swine fever virus is greatly maintained;

3. The live classical swine fever vaccine prepared according to the present invention can be preserved for three months at 37° C. and for one year at 25° C.

4. The vaccine prepared according to the present invention has the dried foam appearance and presents the glass-layer like structure under the scanning electron microscope, has the glass transition temperature up to more than 50° C. and higher than that of the conventional lyophilized vaccine by more than 30° C.

DETAILED DESCRIPTION

Figure 1:
FIG. 1 illustrates an appearance of a live classical swine fever vaccine (dried foam appearance)
Figure 2:
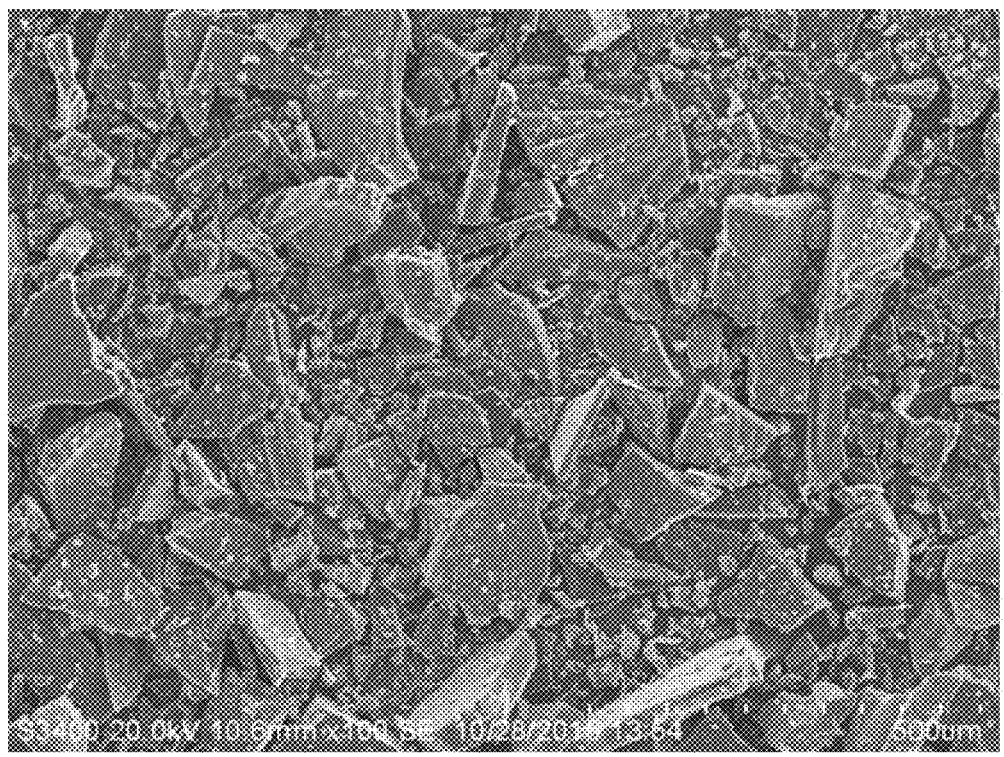
FIG. 2 is a scanning electron microscope photograph of the live classical swine fever vaccine (glass-layer like structure).

The following embodiments further describe the present invention in detail only, but do not constitute any limitation to the present invention.

First Embodiment Preparation of Thermostable Formula 1 and Live Classical Swine Fever Vaccine 1

Unless otherwise specified, the percentages in this embodiment are percentages by weight.

Formulation of thermostable formula 1:

| | |
|---|---|
| Raffinose | 1.0% |
| Maltose | 10.0% |
| Saccharose | 15.0% |
| Lactose | 5.0% |
| Glucose | 1.0% |
| Polysorbate 80 | 0.1% |

-continued

| | |
|---|---|
| Polyethylene glycol 8000 | 0.5% |
| Tyrosine | 3.0% |
| Silk fibroin | 3.0% |
| Water for injection | 61.4% |

Specific preparation steps of the thermostable formula 1 were as follows: raffinose, maltose, saccharose, lactose, glucose and polysorbate 80 were dissolved in water and sterilized by high-pressure steam sterilization (110° C., 20 min); polyethylene glycol 8000, tyrosine and silk fibroin were dissolved in water, and sterilized by 0.22 μm filtration; and a sterilized part by high-pressure and a sterilized part by filtration were mixed in equal volume, and then supplemented with water for injection, to obtain the thermostable formula 1.

Preparation of the live classical swine fever vaccine 1: the thermostable formula 1 was mixed with a classical swine fever virus solution (C strain, a virus content of $50 \times 10^4$ RID/mL) at a volume ratio of 3:1, the mixture was sub-packaged into 7 mL penicillin bottles with 1 mL per bottle, and after half-plugged with a butyl rubber stopper, the mixture was place into a lyophilization cabinet for gradient vacuum drying, to obtain the live classical swine fever vaccine 1.

Specific steps of the gradient vacuum drying were as follows: the live classical swine fever vaccine solution was balanced for 0.5 hour at a normal temperature and a normal pressure, maintained for 0.5 hour at a vacuum degree of 500 mBar and a temperature of 20° C., maintained for 1 hour at a vacuum degree of 500 mBar and a temperature of 20° C., maintained for 0.5 hour at a vacuum degree of 80 mBar and a temperature of 25° C., maintained for 12 hours at a vacuum degree of 0.05 mBar and a temperature of 40° C., and maintained for 24 hours at a vacuum degree of 0.01 mBar and a temperature of 40° C., to obtain the dried live classical swine fever vaccine 1.

Second Embodiment Preparation of Thermostable Formula 2 and Live Classical Swine Fever Vaccine 2

Unless otherwise specified, the percentages in this embodiment are percentages by weight.

Formulation of thermostable formula 2:

| | |
|---|---|
| Raffinose | 5.0% |
| Maltose | 5.0% |
| Saccharose | 30.0% |
| Lactose | 1.0% |
| Glucose | 5.0% |
| Polysorbate 80 | 1.5% |
| Polyethylene glycol 8000 | 0.1% |
| Tyrosine | 0.5% |
| Silk fibroin | 6.0% |
| Water for injection | 45.9% |

Specific preparation steps of the thermostable formula 2 were as follows: raffinose, maltose, saccharose, lactose, glucose and polysorbate 80 were dissolved in water and sterilized by high-pressure steam sterilization; polyethylene glycol 8000, tyrosine and silk fibroin were dissolved in water, and sterilized by filtration; and a sterilized part by high-pressure and a sterilized part by filtration were mixed in equal volume, and then supplemented with water for injection, to obtain the thermostable formula 2.

Preparation of the live classical swine fever vaccine 2: the thermostable formula 2 was mixed with a classical swine fever virus solution (C strain, a virus content of $50\times10^4$ RID/mL) at a volume ratio of 1:1, the mixture was sub-packaged into 7 mL penicillin bottles with 1 mL per bottle, and after half-plugged with a butyl rubber stopper, the mixture was place into a lyophilization cabinet for gradient vacuum drying, to obtain the live classical swine fever vaccine 2.

Specific steps of the gradient vacuum drying were as follows: the live classical swine fever vaccine solution was balanced for 1 hour at a normal temperature and a normal pressure, maintained for 1 hour at a vacuum degree of 800 mBar and a temperature of 10° C., maintained for 0.5 hour at a vacuum degree of 80 mBar and a temperature of 10° C., maintained for 2 hours at a vacuum degree of 50 mBar and a temperature of 15° C., maintained for 12 hours at a vacuum degree of 0.02 mBar and a temperature of 20° C., and maintained for 24 hours at a vacuum degree of 0.001 mBar and a temperature of 20° C., to obtain the dried live classical swine fever vaccine 2.

Third Embodiment Preparation of Thermostable Formula 3 and Live Classical Swine Fever Vaccine 3

Unless otherwise specified, the percentages in this embodiment are percentages by weight.

Formulation of thermostable formula 3:

| | |
|---|---|
| Raffinose | 2.5% |
| Maltose | 7.5% |
| Saccharose | 22.5% |
| Lactose | 2.5% |
| Glucose | 2.5% |
| Polysorbate 80 | 0.75% |
| Polyethylene glycol 8000 | 0.25% |
| Tyrosine | 1.5% |
| Silk fibroin | 4.5% |
| Water for injection | 55.5% |

Specific preparation steps of the thermostable formula 3 were as follows: raffinose, maltose, saccharose, lactose, glucose and polysorbate 80 were dissolved in water and sterilized by high-pressure steam sterilization; polyethylene glycol 8000, tyrosine and silk fibroin were dissolved in water, and sterilized by filtration; and a sterilized part by high-pressure and a sterilized part by filtration were mixed in equal volume, and then supplemented with water for injection, to obtain the thermostable formula 3.

Preparation of the live classical swine fever vaccine 3: the thermostable formula 3 was mixed with a classical swine fever virus solution (C strain, a virus content of $50\times10^4$ RID/mL) at a volume ratio of 3:1, the mixture was sub-packaged into 7 mL penicillin bottles with 1 mL per bottle, and after half-plugged with a butyl rubber stopper, the mixture was place into a lyophilization cabinet for gradient vacuum drying, to obtain the live classical swine fever vaccine 3.

Specific steps of the gradient vacuum drying were as follows: the live classical swine fever vaccine solution was balanced for 2 hours at a normal temperature and a normal pressure, maintained for 0.7 hour at a vacuum degree of 700 mBar and a temperature of 5° C., maintained for 0.5 hour at a vacuum degree of 300 mBar and a temperature of 10° C., maintained for 2 hours at a vacuum degree of 30 mBar and a temperature of 25° C., maintained for 12 hours at a vacuum degree of 0.01 mBar and a temperature of 25° C., and maintained for 12 hours at a vacuum degree of 0.001 mBar and a temperature of 25° C., to obtain the dried live classical swine fever vaccine 3.

Fourth Embodiment Preparation of Thermostable Formula 4 and Live Classical Swine Fever Vaccine 4

Unless otherwise specified, the percentages in this embodiment are percentages by weight.

Formulation of thermostable formula 4:

| | |
|---|---|
| Raffinose | 1.5% |
| Maltose | 6.0% |
| Saccharose | 25.0% |
| Lactose | 4.0% |
| Glucose | 4.0% |
| Polysorbate 80 | 0.5% |
| Polyethylene glycol 8000 | 0.4% |
| Tyrosine | 2.0% |
| Silk fibroin | 5.0% |
| Water for injection | 51.6% |

Specific preparation steps of the thermostable formula 4 were as follows: raffinose, maltose, saccharose, lactose, glucose and polysorbate 80 were dissolved in water and sterilized by high-pressure steam sterilization; polyethylene glycol 8000, tyrosine and silk fibroin were dissolved in water, and sterilized by filtration; and a sterilized part by high-pressure and a sterilized part by filtration were mixed in equal volume, and then supplemented with water for injection, to obtain the thermostable formula 3.

Preparation of the live classical swine fever vaccine 4: the thermostable formula 4 was mixed with a classical swine fever virus solution (C strain, a virus content of $50\times10^4$ RID/mL) at a volume ratio of 3:1, the mixture was subpackaged into 7 mL penicillin bottles with 1 mL per bottle, and after half-plugged with a butyl rubber stopper, the mixture was place into a lyophilization cabinet for gradient vacuum drying, to obtain the live classical swine fever vaccine 4.

Specific steps of the gradient vacuum drying were as follows: the live classical swine fever vaccine solution was balanced for 0.5 hour at a normal temperature and a normal pressure, maintained for 0.5 hour at a vacuum degree of 500 mBar and a temperature of 15° C., maintained for 2 hours at a vacuum degree of 80 mBar and a temperature of 15° C., maintained for 1 hour at a vacuum degree of 50 mBar and a temperature of 20° C., maintained for 12 hours at a vacuum degree of 0.05 mBar and a temperature of 20° C., and maintained for 18 hours at a vacuum degree of 0.01 mBar and a temperature of 25° C., to obtain the dried live classical swine fever vaccine 4.

Fifth Embodiment Preparation of Thermostable Formula 5 and Live Classical Swine Fever Vaccine 5

Unless otherwise specified, the percentages in this embodiment are percentages by weight.

Formulation of thermostable formula 5:

| | |
|---|---|
| Raffinose | 4.0% |
| Maltose | 9.0% |
| Saccharose | 20.0% |

-continued

| | |
|---|---|
| Lactose | 2.0% |
| Glucose | 2.0% |
| Polysorbate 80 | 1.0% |
| Polyethylene glycol 8000 | 0.2% |
| Tyrosine | 1.0% |
| Silk fibroin | 4.0% |
| Water for injection | 56.8% |

Specific preparation steps of the thermostable formula 5 were as follows: raffinose, maltose, saccharose, lactose, glucose and polysorbate 80 were dissolved in water and sterilized by high-pressure steam sterilization; polyethylene glycol 8000, tyrosine and silk fibroin were dissolved in water, and sterilized by filtration; and a sterilized part by high-pressure and a sterilized part by filtration were mixed in equal volume, and then supplemented with water for injection, to obtain the thermostable formula 5.

Preparation of the live classical swine fever vaccine 5: the thermostable formula 5 was mixed with a classical swine fever virus solution (C strain, a virus content of $50\times10^4$ RID/mL) at a volume ratio of 2:1, the mixture was subpackaged into 7 mL penicillin bottles with 1 mL per bottle, and after half-plugged with a butyl rubber stopper, the mixture was place into a lyophilization cabinet for gradient vacuum drying, to obtain the live classical swine fever vaccine 5.

Specific steps of the gradient vacuum drying were as follows: the live classical swine fever vaccine solution was balanced for 0.5 hour at a normal temperature and a normal pressure, maintained for 0.5 hour at a vacuum degree of 800 mBar and a temperature of 30° C., maintained for 2 hours at a vacuum degree of 80 mBar and a temperature of 35° C., maintained for 1 hour at a vacuum degree of 50 mBar and a temperature of 40° C., maintained for 12 hours at a vacuum degree of 0.05 mBar and a temperature of 30° C., and maintained for 18 hours at a vacuum degree of 0.01 mBar and a temperature of 30° C., to obtain the dried live classical swine fever vaccine 5.

Sixth Embodiment Preparation of Thermostable Formula 6 and Live Classical Swine Fever Vaccine 6

Unless otherwise specified, the percentages in this embodiment are percentages by weight.

Formulation of thermostable formula 6:

| | |
|---|---|
| Raffinose | 3.0% |
| Maltose | 8.0% |
| Saccharose | 28.0% |
| Lactose | 3.0% |
| Glucose | 1.0% |
| Polysorbate 80 | 0.6% |
| Polyethylene glycol 8000 | 0.2% |
| Tyrosine | 1.0% |
| Silk fibroin | 3.0% |
| Water for injection | 52.2% |

Specific preparation steps of the thermostable formula 6 were as follows: raffinose, maltose, saccharose, lactose, glucose and polysorbate 80 were dissolved in water and sterilized by high-pressure steam sterilization; polyethylene glycol 8000, tyrosine and silk fibroin were dissolved in water, and sterilized by filtration; and a sterilized part by high-pressure and a sterilized part by filtration were mixed in equal volume, and then supplemented with water for injection, to obtain the thermostable formula 6.

Preparation of the live classical swine fever vaccine 6: the thermostable formula 5 was mixed with a classical swine fever virus solution (C strain, a virus content of $50 \times 10^4$ RID/mL) at a volume ratio of 1:1, the mixture was sub-packaged into 7 mL penicillin bottles with 1 mL per bottle, and after half-plugged with a butyl rubber stopper, the mixture was place into a lyophilization cabinet for gradient vacuum drying, to obtain the live classical swine fever vaccine 6.

Specific steps of the gradient vacuum drying were as follows: the live classical swine fever vaccine solution was balanced for 0.5 hour at a normal temperature and a normal pressure, maintained for 1 hour at a vacuum degree of 500 mBar and a temperature of 25° C., maintained for 2 hours at a vacuum degree of 80 mBar and a temperature of 25° C., maintained for 1 hour at a vacuum degree of 50 mBar and a temperature of 30° C., maintained for 8 hours at a vacuum degree of 0.05 mBar and a temperature of 30° C., and maintained for 24 hours at a vacuum degree of 0.01 mBar and a temperature of 35° C., to obtain the dried live classical swine fever vaccine 6.

Seventh Embodiment Control Thermostable Formula 1

A specific preparation method for the control thermostable formula 1 (disclosed in CN103341176A) was as follows.

(1) Preparation of a solution A: 3 g NZ-amine (NZ amine [commercial] NZ amine [enzymatic hydrolysate of casein]), 0.375 g glutamic acid monopotassium salt (CAS: 6382-01-0), 25 g saccharose and 1.875 g lactoalbumin hydrolysate were weighed, the components above were dissolved in 100 mL water for injection in sequence, and the mixture was shaken well after full dissolution, and was set aside at 2° C. to 8° C. after filtration with 0.22 μm filter membrane and sterilization;

(2) preparation of a solution B: 20 g hydrolyzed gelatin was fully dissolved in 100 mL water for injection at 70° C. to 80° C., and then the mixture was sterilized for 30 minutes at 121° C. and 15 Pounds under high pressure, and was preserved at 37° C. after sterilization; and (3) the solution A and the solution B were proportioned according to a ratio of 4:1, and were evenly mixed to obtain a heat-resistant lyophilized protective agent, wherein a mass volume percentage concentration of each component was as follows: 2.4% NZ-amine, 0.3% glutamic acid monopotassium salt, 20% saccharose, 1.5% lactoalbumin hydrolysate and 4% hydrolyzed gelatin.

Control thermostable formula 1: a control heat-resistant lyophilized protective agent 2 was mixed with a classical swine fever virus antigen solution (C strain, a virus content of $50\times10^4$ RID/mL) according to a volume ratio of 1:4, then the mixture was sub-packaged into 7 mL penicillin bottles with 1 mL per bottle, half-plugged with a butyl rubber stopper, and then placed into a lyophilization cabinet.

Specific lyophilization steps were as follows: the mixed solution was placed into the lyophilization cabinet, a pre-freezing temperature was selected to be −50° C., low-temperature holding time was 2 hours during pre-freezing, the temperature was controlled to be −15° C. during early pre-freezing period, and the mixed solution was quickly frozen after the product released analytical heat; a product temperature during a sublimation period was −33° C., a plate layer temperature was set as −8° C., and sublimation time was 11 hours; and an analysis temperature was 26° C., analysis time was 4 hours, the whole lyophilization process was 24 hours, and the mixed solution was taken out of the cabinet and plugged, so as to obtain the control live classical swine fever vaccine 1.

Eighth Embodiment Control Thermostable Formula 2

A preparation method for the control thermostable formula 2 (disclosed in CN103041399A) was as follows:

| | |
|---|---|
| Trehalose | 68% |
| Glycine | 6% |
| Gelatin | 3% |
| Casamino acid | 6% |
| Polyvinyl pyrrolidone | 6% |
| Glycerinum | 5% |
| Pluronic F-68 | 6% |

Each component was weighed according to the formulation of each thermostable formula to obtain the control thermostable formula 2.

Control thermostable formula 2: the control thermostable formula 2 was mixed with a classical swine fever virus antigen solution (C strain, and a virus content of $50\times10^4$ RID/mL) according to a volume ratio of 1:1, the mixture was sub-packaged into 7 mL penicillin bottles with 1 mL per bottle, and after half-plugged with a butyl rubber stopper, the mixture was place into a lyophilization cabinet.

Specific lyophilization steps were as follows: a control live classical swine fever vaccine 2 was maintained for 4 hours at a normal pressure and a temperature of −52° C., maintained for 18 hours at a vacuum degree of 5.0 mbar and a temperature of −3° C., and maintained for 5 hours at a vacuum degree of 2.5 mbar and a temperature of 20° C., to obtain the control live classical swine fever vaccine 2.

Ninth Embodiment Detection of Physical and Chemical Properties of Live Classical Swine Fever Vaccine A physical property, residual moisture, a glass transition temperature and a vacuum degree of each live classical swine fever vaccine in the first embodiment to the eighth embodiment were measured. The residual moisture and the vacuum degree of the dried vaccine were measured according to the method and standard in the annex of the current Veterinary Pharmacopoeia of the People's Republic of China, and the glass transition temperature was detected by a differential calorimetry scanner. The specific results refer to Table 1. It can be seen from Table 1 that all the results meet the requirements in the annex of the Veterinary Pharmacopoeia of the People's Republic of China, the live classical swine fever vaccines 1 to 6 meet the requirements in terms of the residual moisture and the vacuum degree, and the residual moisture is slightly lower than that of the control live classical swine fever vaccines 1 and 2. The glass transition temperature of the live classical swine fever vaccines 1 to 6 is higher than that of the control live classical swine fever vaccine 1 (traditional lyophilized vaccine) by more than 30° C. The glass transition temperature Tg of the live classical swine fever vaccine 5 is the highest, which is 69±1.68° C.

TABLE 1

Measurement Results of Physical Property and Residual Moisture of Live Classical Swine Fever Vaccine

| Category | Physical property | Residual moisture (<4%, n = 4) | Glass transition temperature Tg° C. | Vacuum degree |
|---|---|---|---|---|
| Live classical swine fever vaccine 1 | Dried foam appearance | 1.33 ± 0.05 | 65 ± 1.58 | Meet the requirements |
| Live classical swine fever vaccine 2 | Dried foam appearance | 1.08 ± 0.22 | 61 ± 1.98 | Meet the requirements |
| Live classical swine fever vaccine 3 | Dried foam appearance | 1.17 ± 0.17 | 63 ± 1.33 | Meet the requirement |
| Live classical swine fever vaccine 4 | Dried foam appearance | 1.51 ± 0.26 | 67 ± 1.17 | Meet the requirements |
| Live classical swine fever vaccine 5 | Dried foam appearance | 1.37 ± 0.12 | 69 ± 1.68 | Meet the requirements |
| Live classical swine fever vaccine 6 | Dried foam appearance | 1.27 ± 0.09 | 65 ± 1.27 | Meet the requirement |
| Control live classical swine fever vaccine 1 | Loose sponge appearance | 2.55 ± 0.22 | 32 ± 1.25 | Meet the requirements |
| Control live classical swine fever vaccine 2 | Dried foam appearance | 2.38 ± 0.15 | 51 ± 2.25 | Meet the requirements |

Tenth Embodiment Measurement of Heat Resistance of Live Classical Swine Fever Vaccine Virus contents of all the live classical swine fever vaccines in the first embodiment to the eighth embodiment before and after being dried, stored for 10 days, 30 days, 60 days, 90 days and 120 days at 37° C., and stored for 1 month, 3 months, 6 months, 9 months, 12 months and 15 months at 25° C. were measured. The virus content detection method of the live classical swine fever vaccine is subjected to the current Regulations on Veterinary Biological Products of the People's Republic of China. Table 2 shows the measurement results of the virus contents of the live classical swine fever vaccines after long-term storage at 37° C.; and Table 3 shows the measurement results of the virus contents of the live classical swine fever vaccines after long-term storage at 25° C.

In Table 2, drying loss refers to a virus content difference of the vaccines before drying and 0 d after being dried. Heat resistance loss refers to a virus content difference of the vaccines 0 d after being dried and stored for different days at 37° C.

It can be seen from Table 2 that the virus content losses of the live classical swine fever vaccines 1 to 6 in the drying process range from 0.4 to 0.52 Lg RID/mL; after storage for 10 days at 37° C., the virus content losses are all less than or equal to 0.3 Lg RID/mL, and after storage for 90 days at 37° C., the virus content losses range from 0.88 to 1.0 Lg RID/mL. The virus content losses of the live classical swine fever vaccines 1 to 6 in the heat-resistant process are all less than that of the control heat-resistant live classical swine fever vaccine. The live classical swine fever vaccine 4 and the live classical swine fever vaccine 5 have the best heat resistance, the heat resistance losses of which are both 1.22 Lg after being stored for 120 days at 37° C.

TABLE 2

| Category | Virus content ($\times 10^4$ RID/mL) | | | | | | |
|---|---|---|---|---|---|---|---|
| | Before being dried | Dried for 0 day | 10 days at 37° C. | 30 days at 37° C. | 60 days at 37° C. | 90 days at 37° C. | 120 days at 37° C. |
| Live classical swine fever vaccine 1 | 50 | 20 | 12 | 3 | 5 | 2 | 0.5 |
| Live classical swine fever vaccine 2 | 50 | 15 | 12 | 10 | 5 | 2 | 0.5 |
| Live classical swine fever vaccine 3 | 50 | 15 | 10 | 3 | 5 | 1.5 | 0.5 |
| Live classical swine fever vaccine 4 | 50 | 20 | 12 | 3 | 5 | 3 | 1.2 |
| Live classical swine fever vaccine 5 | 50 | 20 | 10 | 3 | 5 | 2.5 | 1.2 |
| Live classical swine fever vaccine 6 | 50 | 20 | 10 | 3 | 5 | 2 | 0.5 |
| Control live classical swine fever vaccine 1 | 50 | 15 | 5 | 0.5 | | | |
| Control live classical swine fever vaccine 2 | 50 | 20 | 10 | 6 | 2 | 0.5 | |

| Category | Virus content loss (Lg RID/mL) | | | | | |
|---|---|---|---|---|---|---|
| | Drying loss | Heat resistance loss | | | | |
| | | 10 days at 37° C. | 30 days at 37° C. | 60 days at 37° C. | 90 days at 37° C. | 120 days at 37° C. |
| Live classical swine fever vaccine 1 | 0.4 | 0.22 | 0.4 | 0.6 | 1.0 | 1.6 |
| Live classical swine fever vaccine 2 | 0.52 | 0.1 | 0.18 | 0.43 | 0.33 | 1.43 |
| Live classical swine fever vaccine 3 | 0.52 | 0.18 | 0.27 | 0.43 | 1.0 | 1.43 |

TABLE 2-continued

| | | | | | | |
|---|---|---|---|---|---|---|
| Live classical swine fever vaccine 4 | 0.4 | 0.22 | 0.4 | 0.6 | 0.82 | 1.22 |
| Live classical swine fever vaccine 5 | 0.4 | 0.3 | 0.4 | 0.6 | 0.9 | 1.22 |
| Live classical swine fever vaccine 6 | 0.4 | 0.3 | 0.4 | 0.6 | 1.0 | 1.6 |
| Control live classical swine fever vaccine 1 | 0.52 | 0.43 | 1.43 | | | |
| Control live classical swine fever vaccine 2 | 0.4 | 0.3 | 0.52 | 1.0 | 1.6 | |

TABLE 3

| | Virus content ($\times 10^4$ RID/mL) | | | | | | |
|---|---|---|---|---|---|---|---|
| Category | Before being dried | Dried for 0 day | 1 month at 25° C. | 3 months at 25° C. | 6 months at 25° C. | 9 months at 25° C. | 12 months at 25° C. | 15 months at 25° C. |
| Live classical swine fever vaccine 1 | 50 | 20 | 10 | 3 | 5 | 4 | 2.0 | 0.5 |
| Live classical swine fever vaccine 2 | 50 | 15 | 12 | 10 | 5 | 2 | 1.5 | 0.5 |
| Live classical swine fever vaccine 3 | 50 | 15 | 10 | 3 | 5 | 3 | 2 | 0.5 |
| Live classical swine fever vaccine 4 | 50 | 20 | 15 | 10 | 8 | 4 | 2 | 1 |
| Live classical swine fever vaccine 5 | 50 | 20 | 12 | 10 | 8 | 5 | 3 | 1 |
| Live classical swine fever vaccine 6 | 50 | 20 | 10 | 3 | 5 | 4 | 2 | 1 |
| Control live classical swine fever vaccine 1 | 50 | 15 | 0.5 | / | / | / | / | / |
| Control live classical swine fever vaccine 2 | 50 | 20 | 2 | 0.5 | / | / | / | / |

| | Virus content loss (Lg RID/mL) | | | | | | |
|---|---|---|---|---|---|---|---|
| | | Heat resistance loss | | | | | |
| Category | Drying loss | 1 month at 25° C. | 3 months at 25° C. | 6 months at 25° C. | 9 months at 25° C. | 12 months at 25° C. | 15 months at 25° C. |
| Live classical swine fever vaccine 1 | 0.4 | 0.3 | 0.4 | 0.6 | 0.7 | 1.0 | 1.6 |
| Live classical swine fever vaccine 2 | 0.52 | 0.1 | 0.13 | 0.48 | 0.33 | 1.0 | 1.48 |
| Live classical swine fever vaccine 3 | 0.52 | 0.13 | 0.27 | 0.48 | 0.7 | 0.83 | 1.48 |
| Live classical swine fever vaccine 4 | 0.4 | 0.12 | 0.3 | 0.4 | 0.7 | 1.0 | 1.3 |
| Live classical swine fever vaccine 5 | 0.4 | 0.22 | 0.3 | 0.4 | 0.6 | 0.82 | 1.3 |
| Live classical swine fever vaccine 6 | 0.4 | 0.3 | 0.4 | 0.6 | 0.7 | 1.0 | 1.3 |
| Control live classical swine fever vaccine 1 | 0.52 | 1.48 | / | / | / | / | / |
| Control live classical swine fever vaccine 2 | 0.4 | 1.0 | 1.6 | / | / | / | / |

In Table 3, drying loss refers to a difference between 0 d vaccine virus contents before and after being dried. Heat resistance loss refers to a difference between the vaccine virus contents after the vaccine is dried for 0 day and stored for different days at 25° C.

It can be seen from Table 3 that the virus content losses of the live classical swine fever vaccines 1 to 6 in the drying process range from 0.4 to 0.52 Lg RID/mL; after storage for 6 months at 25° C., the virus content losses are all less than or equal to 0.6 Lg RID/mL, after storage for 12 months at 25° C., the virus content losses range from 0.82 to 1.0 Lg RID/mL; and after storage for 1 month at 25° C., the virus content losses of the control live classical swine fever vaccines 1 and 2 range from 1.0 to 1.48 Lg RID/mL. The virus content losses of the live classical swine fever vaccines 1 to 6 in the heat-resistant process are all less than that of the control heat-resistant live classical swine fever vaccine. The live classical swine fever vaccine 5 has the best heat resistance, the virus content loss is only 0.82 Lg RID/mL when stored for 12 months at 25° C., and this result is correlated with the best heat resistance at highest Tg when stored for 90 days to 120 days at 37° C.

What is claimed is:

1. A preparation method of a thermostable formula, wherein the thermostable formula comprises 1% to 5% of raffinose, 5% to 10% of maltose, 15% to 30% of saccharose, 1% to 5% of lactose, 1% to 5% of glucose, 0.1% to 1.5% of polysorbate 80, 0.1% to 0.5% of polyethylene glycol 8000, 0.5% to 3% of tyrosine, 3% to 6% of silk fibroin by weight; the preparation method comprising the following steps of:
1) dissolving the raffinose, the maltose, the saccharose, the lactose, the glucose and the polysorbate 80 in water and carrying out sterilization by high-pressure steam sterilization to obtain a solution 1;
2) dissolving the polyethylene glycol 8000, the tyrosine and the silk fibroin in water, and carrying out sterilization by filtration to obtain a solution 2; and
3) mixing the solution 1 and the solution 2, and supplementing water to obtain the thermostable formula.

2. A preparation method of a live classical swine fever virus vaccine, wherein a classical swine fever virus solution and the thermostable formula according to claim 1 are uniformly mixed according to a volume ratio of 1:1 to 3:1 to prepare a live classical swine fever virus vaccine solution, and the live classical swine fever virus vaccine is obtained after gradient vacuum drying of the live classical swine fever virus vaccine solution.

3. The preparation method of the live classical swine fever vaccine according to claim 2, wherein the gradient vacuum drying method is as follows: the live classical swine fever virus vaccine solution is balanced for 0.5 hour to 2 hours at a room temperature, maintained for 0.5 hour to 1 hour at a vacuum degree of 500 mBar to 800 mBar and a temperature of 5° C. to 30° C., maintained for 0.5 hour to 2 hours at a vacuum degree of 80 mbar to 500 mbar and a temperature of 10° C. to 35° C., maintained for 0.5 hour to 2 hours at a vacuum degree of 30 mBar to 80 mBar and a temperature of 10° C. to 40° C., maintained for 8 hours to 12 hours at a vacuum degree of 0.01 mbar to 0.05 mbar and a temperature of 20° C. to 40° C., and maintained for 12 hours to 24 hours at a vacuum degree of 0.001 mbar to 0.01 mbar and a temperature of 20° C. to 40° C., to obtain a dried live classical swine fever virus vaccine.

4. The preparation method of the live classical swine fever virus vaccine according to claim 2, wherein the dried live classical swine fever virus vaccine presents a glass-layer like structure under a scanning electron microscope, and a glass transition temperature thereof reaches up to more than 50° C.

5. The preparation method of the live classical swine fever virus vaccine according to claim 2, wherein the glass transition temperature reaches up to 65° C. to 70° C.

6. The preparation method of the live classical swine fever vaccine according to claim 2, wherein the classical swine fever virus in the solution is a CSFV C strain.

7. The preparation method of the thermostable formula according claim 1, wherein the thermostable formula comprises 1.5% to 4% of the raffinose, 6% to 10% of the maltose, 20% to 25% of the saccharose, 2% to 4% of the lactose, 2% to 4% of the glucose, 0.5% to 1% of the polysorbate 80, 0.2% to 0.4% of the polyethylene glycol 8000, 1% to 2% of the tyrosine, 4% to 5% of the silk fibroin by weight.

8. The preparation method of the live classical swine fever virus vaccine according to claim 2, wherein the thermostable formula comprises 1.5% to 4% of the raffinose, 6% to 10% of the maltose, 20% to 25% of the saccharose, 2% to 4% of the lactose, 2% to 4% of the glucose, 0.5% to 1% of the polysorbate 80, 0.2% to 0.4% of the polyethylene glycol 8000, 1% to 2% of the tyrosine, 4% to 5% of the silk fibroin by weight.

* * * * *